United States Patent
Choi et al.

(10) Patent No.: US 10,821,086 B2
(45) Date of Patent: Nov. 3, 2020

(54) MUSCULAR ATROPHY-INDUCING AGENT USING HYPOMETABOLISM-INDUCING SUBSTANCE T1AM, AND USE THEREOF IN TREATING MUSCULAR HYPERTROPHY

(71) Applicant: UNIVERSITY INDUSTRY FOUNDATION, YONSEI UNIVERSITY WONJU CAMPUS, Wonju-si, Gangwon-do (KR)

(72) Inventors: Inho Choi, Wonju-si (KR); Kyoungsook Park, Seoul (KR); Hyun Woo Ju, Seoul (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 289 days.

(21) Appl. No.: 15/576,231

(22) PCT Filed: Jun. 29, 2016

(86) PCT No.: PCT/KR2016/006955
§ 371 (c)(1),
(2) Date: Nov. 21, 2017

(87) PCT Pub. No.: WO2017/003177
PCT Pub. Date: Jan. 5, 2017

(65) Prior Publication Data
US 2018/0140562 A1    May 24, 2018

(30) Foreign Application Priority Data

Jun. 29, 2015 (KR) .................. 10-2015-0091807
Jun. 2, 2016 (KR) .................. 10-2016-0068882

(51) Int. Cl.
| | |
|---|---|
| *A61K 31/00* | (2006.01) |
| *G01N 33/53* | (2006.01) |
| *A61K 31/135* | (2006.01) |
| *A61K 31/7076* | (2006.01) |
| *A61K 33/04* | (2006.01) |
| *A61P 21/00* | (2006.01) |
| *C12N 15/01* | (2006.01) |
| *G01N 33/50* | (2006.01) |
| *A61K 38/08* | (2019.01) |

(52) U.S. Cl.
CPC ........ *A61K 31/135* (2013.01); *A61K 31/7076* (2013.01); *A61K 33/04* (2013.01); *A61K 38/08* (2013.01); *A61P 21/00* (2018.01); *C12N 15/01* (2013.01); *G01N 33/5061* (2013.01)

(58) Field of Classification Search
None
See application file for complete search history.

(56) References Cited

U.S. PATENT DOCUMENTS

| | | |
|---|---|---|
| 6,979,750 B1 | 12/2005 | Scanlan et al. |
| 7,321,065 B2 | 1/2008 | Scanlan et al. |
| 2006/0035980 A1 | 2/2006 | Scanlan et al. |
| 2013/0269046 A1 | 10/2013 | Kinsella et al. |

FOREIGN PATENT DOCUMENTS

| | | |
|---|---|---|
| JP | 2006-162346 A | 6/2006 |
| JP | 2011-220974 A | 11/2011 |
| JP | 2010-276612 A | 12/2019 |
| KR | 10-1112731 B1 | 3/2012 |
| KR | 10-2012-0084500 A | 7/2012 |
| KR | 10-1208741 B1 | 12/2012 |

OTHER PUBLICATIONS

Ju et al, Horm Metab Res, 47:605-610, published online Nov. 5, 2014).*
Haviland et al, Obesity, 21:2538-2544, 2013.*
(Continued)

Primary Examiner — Mark Halvorson
(74) Attorney, Agent, or Firm — Novick, Kim & Lee, PLLC; Jae Youn Kim (57) ABSTRACT

The present invention relates to: a muscular atrophy-inducing agent containing, as an active ingredient, a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$); a method for preparing a muscular atrophy study model comprising inducing muscular atrophy by administering the muscular atrophy-inducing agent; a study model prepared by the method; a screening method for a drug for preventing or treating muscular atrophy using the same; a composition for preventing or treating muscular hypertrophy; and a composition for facial muscle shrinkage. The muscular atrophy study model according to the present invention can provide a study model for an economic muscular atrophy study by using a hypometabolism-inducing substance which can be mass-produced, has an effect which may be usefully used by verification for screening of a drug for preventing or treating muscular atrophy, and can be usefully used as a compositions for preventing or treating muscular hypertrophy and a composition for facial muscle shrinkage through the muscular atrophy effect.

5 Claims, 7 Drawing Sheets

(56) References Cited

OTHER PUBLICATIONS

Assadi-Porter et al, Endocrine Rev, 34:A422, 2013.*
Gwag, Taesik et al., Stress and Signaling Responses of Rat Skeletal Muscle to Brief Endurance Exercise During Hindlimb Unloading: a Catch-Up Process for Atrophied Muscle, Journal, 2009, pp. 537-546, vol. 24.
Ju, Hyunwoo et al., Sustained Torpidity Following Multi-Dose Administration of 3-Iodothyronamine in Mice, Journal, 2011, pp. 853-858, vol. 226-4.
Shimizu, Noriaki et al., Crosstalk between Glucocorticoid Receptor and Nutritional Sensor mTOR in Skeletal, Muscle, Article, 2011, pp. 170-182, vol. 13-2.
Bang, Hyun-Soo et al., The Effects of Vibration on Expression of BDNF and Functional Recovery after Muscle Atrophy Model lead to Spinal Cord Injury, Journal, 2008, pp. 959-969, vol. 17-3, The Korean Society Of Sports Science.
Zucchi, R et al., Trace amine-associated receptors and their ligands, Journal, 2006, pp. 967-978, vol. 149-8.
McClung, J. M. et al., Calpain-1 is required for hydrogen peroxide-induced myotube atrophy, Journal, 2009, pp. C363-C371, vol. 296-2.
Choi, In-Ho et al., Inhibition of muscle atrophy by bioactive substances in space microgravity, Research, 2013, pp. 1-68.
Choi, In-Ho et al., Inhibition of muscle atrophy by bioactive substances in space microgravity, Research, 2011, pp. 1-22.
Bodine et al., Identification of Ubiquit in Ligases Required for Skeletal Muscle Atrophy, Science, 2001, pp. 1704-1708, vol. 294.

* cited by examiner

MUSCULAR ATROPHY-INDUCING AGENT USING HYPOMETABOLISM-INDUCING SUBSTANCE T1AM, AND USE THEREOF IN TREATING MUSCULAR HYPERTROPHY

TECHNICAL FIELD

The present invention relates to a muscular atrophy-inducing agent based on hypometabolism efficacy of 3-iodothyronamine (T1AM) and a composition for preventing or treating muscular hypertrophy including myotonia congenital, calf hypertrophy, myhre syndrome, and myostatin-related muscular hypertrophy, or for facial muscle shrinkage using the hypometabolism-inducing substance.

BACKGROUND ART

The muscular atrophy occurs in various pathological and physiological conditions such as bodily injury, cancer cachexia in cancer patients, muscle aging, long-term bed life, or space flight as well as genetic disorders (e.g., Duchenne muscle dystrophy). Amounts of muscle proteins such as actin and myosin are decreased, and muscle mass and muscle strength are significantly decreased. Accordingly, since the muscular atrophy has an effect on most of activities from simple behaviors to routine tasks, exercises, and even astronaut missions, a pharmacological rehabilitative medical research to treat the muscular atrophy is important.

A first step for treating of the muscular atrophy is to develop an appropriate model to induce the muscular atrophy. As an animal model (in vivo), denervation and hindlimb suspension methods have been mainly used. Treatment methods of dexamethasone which is synthetic glucocorticoid, oxidizing substances (for example, active oxygen such as $H_2O_2$), or the like have been used as drugs. It has been known that the animal model and the drugs activate signaling pathways which are associated with muscle protein catabolism such as activation of forkhead box O (FoxO), increased expression of ubiquitin E3 ligase and proteasome without exception and simultaneously, inhibit signaling pathways (Akt1-S6K) which are associated with muscle protein anabolism (Shimizu et al., 2011). Further, it has been known that the expression of chaperone proteins (e.g., heat shock proteins) that help protein biogenesis, repair of damage, and the like during the muscular atrophy is also decreased (Gwag et al. 2009).

When describing the mechanism of the muscular atrophy-inducing agents, according to recent reports, it is known that the dexamethasone as a steroid hormone-based substance having an anti-inflammatory effect binds to a glucocorticoid receptor (GR) and activates a proteolytic signaling pathway of FoxO-proteasome to induce the muscular atrophy. It is reported that oxidative substances such as hydrogen peroxide damage the sarcoplasmic reticulum membrane and the mitochondrial membrane, and the released $Ca^{2+}$ and cytochrome C accelerate the activation of calpain proteases to induce the muscular atrophy (McClung et al. 2009).

In addition, the muscular hypertrophy is a disease caused when the balance of muscle protein synthesis and degradation breaks down, and as typical examples, there are myotonia congenita, calf hypertrophy, myhre syndrome, myostatin-related muscular hypertrophy, and the like. Among these diseases, particularly, the myostatin-related muscular hypertrophy is a symptom caused by breakdown of a myostatin gene associated with the muscle protein degradation. Myostatin serves to inhibit a muscle protein synthesis pathway (e.g., Akt1-mTOR) and increases the activity of a muscle protein degradation pathway (e.g., SMAD-proteasome), but when this gene is broken, the balance of muscle mass retention is broken and thus the muscular hypertrophy occurs.

Meanwhile, 3-iodothyronamine (T1AM) is a derivative of thyroid hormones T3 and T4 and a hypometabolism-inducing substance that may be generated in the body. It has been found that a pico mole of 3-iodothyronamine is present in most of the rodent tissue samples (brain, liver, heart, kidney, muscle, etc.) and the human blood (Zucchi R et al., 2006). In addition, 3-iodotronamine is a synthesizable substance and a preparing method thereof is disclosed in U.S. Pat. Nos. 6,979,750 and 7,321,065 and Korean Patent Registration No. 1,112,731, which is a prior patent of the inventor of the present application, and the 3-iodotronamine can be mass-produced to be easily used for industrial use.

The present inventors found that muscular atrophy may be induced by treating a hypometabolism-inducing substance according to protein expression levels associated with generation and inhibition of muscle proteins and a change in size of myotube cells and intend to provide a new concept of muscular atrophy study model which is different from existing methods using the hypometabolism-inducing substance, and a muscle hyperthrophy treating agent through a muscular atrophy inhibition effect or a composition for facial muscle shrinkage usable for Botox.

PRIOR ARTS

Patent Document (Patent Document 1) US Patent Publication No. 2013-0269046

DISCLOSURE

Technical Problem

An object of the present invention is to provide a muscular atrophy study model as a novel muscular atrophy inducing method which is different from a denervation method, a hindlimb suspension method, and a method for treating dexamethasone as synthetic glucorticoid, an oxidizing agent (e.g., active oxygen such as $H_2O_2$), or the like in the related art. Herein, the study model may include cell, tissue, and animal models.

Another object of the present invention is to provide a pharmaceutical composition or a health food for preventing or treating muscular hypertrophy using a hypometabolism-inducing substance of the present invention.

Yet another object of the present invention is to provide a composition for facial muscle shrinkage usable for Botox using a hypometabolism-inducing substance of the present invention.

Technical Solution

In order to achieve the objects, an exemplary embodiment of the present invention provides a muscular atrophy-inducing agent containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$), by targeting an animal model, a muscular atrophy study model including inducing muscular atrophy by administering the muscular atrophy-inducing agent to cells and animals, and a drug screening method for preventing or treating muscular atrophy based on the muscular atrophy study model.

Another exemplary embodiment of the present invention provides a pharmaceutical composition for preventing or treating muscular hypertrophy using the hypometabolism-inducing substance.

Yet another exemplary embodiment of the present invention provides a health food for preventing or treating muscular hypertrophy using the hypometabolism-inducing substance.

Still another exemplary embodiment of the present invention provides a composition for facial muscle shrinkage using the hypometabolism-inducing substance.

Advantageous Effects

According to the present invention, the muscular atrophy inducing model may provide an economic muscular atrophy study model by using a hypometabolic compound enabling mass production and may be usefully used by verification for screening a drug for preventing or treating muscular atrophy. Further, since the hypometabolic compound significantly activates muscle protein degradation, the hypometabolic compound may be usefully used as a drug for treating muscular hypertrophy or a composition for facial muscle shrinkage.

MODES OF THE INVENTION

The present invention relates to a muscular atrophy-inducing agent containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$), by targeting an animal model, a method for preparing a muscular atrophy study model including inducing muscular atrophy by treating or administering the muscular atrophy-inducing agent, a sturdy model prepared according to the method, a method for using drug screening for preventing or treating muscular atrophy using the muscular atrophy study model, and a for preventing or treating muscular hypertrophy using the hypometabolic substance as an active ingredient or a composition for facial muscle shrinkage using the hypometabolic substance as an active ingredient. The present inventors found the fact that the hypometabolism-inducing substance inhibited a muscle protein synthesis mechanism and activated a degradation mechanism through related protein expression and a change in size of myotubes and completed the present invention.

Hereinafter, the present invention will be described in more detail.

The present invention provides a muscular atrophy-inducing agent containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

In one embodiment of the present invention, the hypometabolism-inducing substance may be more particularly 3-iodothyronamine (T1AM).

In one embodiment of the present invention, in the study model, as a cell line, a muscle cell line may be used, general muscle cell lines or muscle fibers used in the art may be used, and for example, C2C12 muscle cells and the like may be used.

In one embodiment of the present invention, in the study model, the animal may be vertebrate animals, more specifically vertebrate animals except for humans, and for example, may include rodents including mice, rats, and hamsters, rabbits, horses, cows, dogs, cats, monkeys, guinea pigs, and the like.

Further, the present invention provides a method for preparing a muscular atrophy study model including inducing muscular atrophy by administering to a normal animal a hypometabolism-inducing substance selected from the group consisting of 3-iodothyronamine (T1AM), [D-Ala2, D-Leu5] enkephalin (DADLE), 5'-adenosine monophosphate (5'-AMP), and hydrogen sulfide ($H_2S$).

In one embodiment of the present invention, the hypometabolism-inducing substance may be more particularly 3-iodothyronamine (T1AM), and a dose of the T1AM may be appropriately adjusted. For example, when T1AM is administered intraperitoneally, if the dose of T1AM is less than 10 mg/kg per unit weight (kg) of an administered animal, it is difficult to cause muscular atrophy, and if the dose exceeds 500 mg/kg, the animal dies. As a result, the dose of T1AM may be 10 to 500 mg/kg, more specifically 20 to 250 mg/kg, and more specifically 25 to 100 mg/kg, per unit body weight (kg) of animal, but may be appropriately adjusted according to the condition of the animal and experimental conditions.

In one embodiment of the present invention, the treatment concentration in the cells may be 0.1 μM to 1000 μM, but may be appropriately adjusted according to the amount of cells, conditions of the cells, and experimental conditions.

In one embodiment of the present invention, the administration of the hypometabolism-inducing substance may be performed by a general administration method, such as oral administration, intraperitoneal administration, intravenous administration, intramuscular administration, subcutaneous administration, or intradermal administration, but the administration method is not limited thereto. Further, the hypometabolism-inducing substance may be administered by any device which is movable to a target cell as an active substance.

In one embodiment of the present invention, the number of dose times of the hypometabolism-inducing substance may be one to two or more times per day, but the number of dose times may be controlled according to the dose of the hypometabolism-inducing substance.

In one embodiment of the present invention, the degree of muscular atrophy in the muscular atrophy animal model may be adjusted by controlling a dose of the hypometabolism-inducing substance or an exposure time in vivo of the hypometabolism-inducing substance, and this may be performed based on the degree of muscular atrophy increasing in proportion to the dose or the exposure time in vivo.

Further, the present invention provides a muscular atrophy cell model or animal model prepared by the method.

In one embodiment of the present invention, the muscular atrophy study model may show the following results from (a) to (j) as compared to a normal by the administration of hypometabolism-inducing substance, which was confirmed by a muscle cell experiment:

(a) Decrease in size of myotubes or size of muscle;
(b) Increase in expression ratio of p-AMPK/AMPK;
(c) Decrease in expression ratio of p-Akt1/Akt1;
(d) Decrease in expression ratio of p-S6K/S6K;
(e) Decrease in expression ratio of p-FoxO1/FoxO1;
(f) Decrease in expression ratio of p-FoxO3/FoxO3;
(g) Increase in expression level of MuRF1;
(h) Increase in activity of proteasome;
(i) Decrease in expression level of heat shock protein 72 (HSP72); and
(j) Decrease in expression level of αB-crystallin Accordingly, the muscular atrophy study model may have at least one characteristic selected from the group consisting of (a) a decrease in size of myotubes or size of muscle; (b) an increase in expression ratio of p-AMPK/AMPK; (c) a decrease in expression ratio of p-Akt1/Akt1; (d) a decrease in expression ratio of p-S6K/S6K; (e) a decrease in expression ratio of p-FoxO1/FoxO1; (f) a decrease in expression ratio of p-FoxO3/FoxO3; (g) an increase in expression level of MuRF1; (h) an increase in activity of proteasome; (i) a decrease in expression level of heat shock protein 72 (HSP72); and (j) a decrease in expression level of αB-crystallin, as compared to a normal.

In one embodiment of the present invention, (a) to (j) may be characteristics compared to the normal after 5 to 10 days of administration of the hypometabolism-inducing substance.

In one embodiment of the present invention, when 0.1 μM to 1000 μM of T1MA as the hypometabolism-inducing substance is treated to the myotubes, with respect to (a) above, the size of the myotubes may be decreased by 0.01 to 0.20 times as compared to the size of the normal myotubes. With respect to (b) above, the expression ratio of p-AMPK/AMPK in the muscular atrophy study model may be increased by 0.01 to 2.5 times as compared to the expression ratio of p-AMPK/AMPK in the normal model. With respect to (c) above, the expression ratio of p-Akt1/Akt1 in the muscular atrophy study model may be decreased by 0.01 to 1.0 times as compared to the expression ratio of p-Akt1/Akt1 in the normal model. With respect to (d) above, the expression ratio of p-S6K/S6K in the muscular atrophy study model may be decreased by 0.01 to 1.0 times as compared to the expression ratio of p-S6K/S6K in the normal model. With respect to (e) above, the expression ratio of p-FoxO1/FoxO1 in the muscular atrophy study model may be decreased by 0.01 to 1.0 times as compared to the expression ratio of p-FoxO1/FoxO1 in the normal model. With respect to (f) above, the expression ratio of p-FoxO3/FoxO3 in the muscular atrophy study model may be decreased by 0.01 to 0.8 times as compared to the expression ratio of p-FoxO3/FoxO3 in the normal model. With respect to (g) above, the expression level of MuRF1 in the muscular atrophy study model may be increased by 0.01 to 2.5 times as compared to the expression level of MuRF1 in the normal model. With respect to (h) above, the activity of proteasome in the muscular atrophy study model may be increased by 0.01 to 2.0 times as compared to the activity of proteasome in the normal model. The proteasome may be 26S proteasome, and the activity thereof can be measured using a method known as a method for measuring the activity of proteasome. For example, the activity of proteasome may be analyzed through chemotrypsin-like activity. With respect to (i) above, the expression level of heat shock protein 72 (HSP72) in the muscular atrophy study model may be increased by 0.01 to 0.15 times as compared to the expression level of heat shock protein 72 (HSP72) in the normal model. With respect to (j) above, the expression level of αB-crystallin in the muscular atrophy study model may be decreased by 0.01 to 1.0 times as compared to the expression level of αB-crystallin in the normal model. The expression levels of AMPK, phospho-AMPK (p-AMPK), FoxO1, p-FoxO1, FoxO3, p-FoxO3, Akt1, p-Akt1, S6K, p-S6K, MuRF1, HSP72, and αB-crystallin in (b) to (g), (i), and (j) may be measured by using methods known as a protein analysis method. For example, the expression levels may be measured by an immunoblotting method.

The muscular atrophy study model may be used as a study model for accurate muscular atrophy studies, but may also be useful as verification for screening of a drug of preventing or treating muscular atrophy.

Accordingly, the present invention provides a method for screening a drug for treating muscular atrophy including: treating a candidate substance in the muscular atrophy study model; and determining the candidate substance as the drug for treating muscular atrophy by evaluating the improved or treated degree of the muscular atrophy in the sturdy model treated with the candidate substance.

In one embodiment of the present invention, the candidate substance is a substance capable of treating muscular atrophy and includes chemicals, oligonucleotides, peptides, genes, proteins, and the like, without limitation.

In one embodiment of the present invention, the degree of improvement or treatment of muscular atrophy may be evaluated by comparing at least one of the following indicators (1) to (10) with that of the control:

(1) Size of myotubes or size of muscle;
(2) Expression ratio of p-AMPK/AMPK;
(3) Expression ratio of p-Akt1/Akt1;
(4) Expression ratio of p-S6K/S6K;
(5) Expression ratio of p-FoxO1/FoxO1;
(6) Expression ratio of p-FoxO3/FoxO3;
(7) Expression level of MuRF1;
(8) Activity of proteasome;
(9) Expression level of heat shock protein 72 (HSP72); and
(10) Expression level of αB-crystallin With respect to indicator (1) above, the degree of improvement or treatment of muscular atrophy may be evaluated by comparing changes in the size of the myotubes or the size of the muscle in the group treated with the candidate substance and the control. When the size of the myotubes or the muscle in the group treated with the candidate substance is increased compared to that of the control, the candidate substance may be determined as a drug for treating muscular atrophy.

With respect to indicator (2) above, the degree of improvement or treatment of muscular atrophy may be evaluated by comparing expression ratios of p-AMPK/AMPK in the group treated with the candidate substance and the control. When the expression ratio of p-AMPK/AMPK in the group treated with the candidate substance is decreased compared to that of the control, the candidate substance may be determined as a drug for treating muscular atrophy.

With respect to indicator (3) above, the degree of improvement or treatment of muscular atrophy may be evaluated by comparing expression ratios of p-Akt1/Akt1 in the group treated with the candidate substance and the control. When the expression ratio of p-Akt1/Akt1 in the group treated with the candidate substance is increased compared to that of the control, the candidate substance may be determined as a drug for treating muscular atrophy.

With respect to indicator (4) above, the degree of improvement or treatment of muscular atrophy may be evaluated by comparing expression ratios of p-S6K/S6K in the group treated with the candidate substance and the control. When the expression ratio of p-S6K/S6K in the group treated with the candidate substance is increased compared to that of the control, the candidate substance may be determined as a drug for treating muscular atrophy.

With respect to indicator (5) above, the degree of improvement or treatment of muscular atrophy may be evaluated by comparing expression ratios of p-FoxO1/FoxO1 in the group treated with the candidate substance and the control. When the expression ratio of p-FoxO1/FoxO1 in the group treated with the candidate substance is increased compared to that of the control, the candidate substance may be determined as a drug for treating muscular atrophy.

With respect to indicator (6) above, the degree of improvement or treatment of muscular atrophy may be evaluated by comparing expression ratios of p-FoxO3/FoxO3 in the group treated with the candidate substance and the control. When the expression ratio of p-FoxO3/FoxO3 in the group treated with the candidate substance is increased compared to that of the control, the candidate substance may be determined as a drug for treating muscular atrophy.

With respect to indicator (7) above, the degree of improvement or treatment of muscular atrophy may be evaluated by comparing expression levels of MuRF1 in the group treated with the candidate substance and the control. When the expression level of MuRF1 in the group treated with the candidate substance is decreased compared to that of the control, the candidate substance may be determined as a drug for treating muscular atrophy.

With respect to indicator (8) above, the degree of improvement or treatment of muscular atrophy may be evaluated by comparing proteasome activities in the group treated with the candidate substance and the control. When the activity of proteasome in the group treated with the candidate substance is decreased compared to that of the control, the candidate substance may be determined as a drug for treating muscular atrophy.

With respect to indicator (9) above, the degree of improvement or treatment of muscular atrophy may be evaluated by comparing expression levels of hot shock protein 72 (HSP72) in the group treated with the candidate substance and the control. When the expression level of hot shock protein 72 (HSP72) in the group treated with the candidate substance is increased compared to that of the control, the candidate substance may be determined as a drug for treating muscular atrophy.

With respect to indicator (10) above, the degree of improvement or treatment of muscular atrophy may be evaluated by comparing expression levels of αB-crystallin in the group treated with the candidate substance and the control. When the expression level of αB-crystallin in the group treated with the candidate substance is increased compared to that of the control, the candidate substance may be determined as a drug for treating muscular atrophy.

Accordingly, in the determining, when the group treated with the candidate substance is compared to the control, in the case of at least one result selected from the group consisting of an increase in size of myotubes or size of muscle; a decrease in expression ratio of p-AMPK/AMPK; an increase in expression ratio of p-Akt1/Akt1; an increase in expression ratio of p-S6K/S6K; an increase in expression ratio of p-FoxO1/FoxO1; an increase in expression ratio of p-FoxO3/FoxO3; a decrease in expression level of MuRF1; a decrease in activity of proteasome; an increase in expression level of heat shock protein 72 (HSP72); and an increase in expression level of αB-crystallin, the candidate substance may be determined as a drug for treating muscular atrophy.

The control refers to a group treated with an excipient of the drug for treating muscular atrophy instead of the candidate substance, and for example, the control may be a group consisting of dimethyl sulfoxide (DMSO), physiological saline, sterilized distilled water, carboxymethyl cellulose or phosphate buffered saline (PBS).

The present invention provides a screening method for a drug for preventing muscular atrophy including: treating or administering a candidate substance to normal cells or a normal animal; treating or administering a hypometabolism-inducing substance to the cells or the animal; and determining the candidate substance as the drug for preventing muscular atrophy by evaluating the degree of muscular atrophy in the cells or the animal treated with the hypometabolism-inducing substance.

In one embodiment of the present invention, the candidate substance is the same as described above.

In one embodiment of the present invention, the degree of muscular atrophy may be evaluated by comparing at least one of the following indicators (1) to (10) with that of the control:

(1) Size of myotubes or size of muscle;
(2) Expression ratio of p-AMPK/AMPK;
(3) Expression ratio of p-Akt1/Akt1;
(4) Expression ratio of p-S6K/S6K;
(5) Expression ratio of p-FoxO1/FoxO1;
(6) Expression ratio of p-FoxO3/FoxO3;
(7) Expression level of MuRF1;
(8) Activity of proteasome;
(9) Expression level of heat shock protein 72 (HSP72); and
(10) Expression level of αB-crystallin With respect to indicator (1) above, the degree of muscular atrophy may be evaluated by comparing changes in the size of the myotubes or the size of the muscle in the group treated with the candidate substance and the control. When the size of the myotube or the muscle in the group treated with the candidate substance is increased compared to that of the control, the candidate substance may be determined as a drug for preventing muscular atrophy.

With respect to indicator (2) above, the degree of muscular atrophy may be evaluated by comparing expression ratios of p-AMPK/AMPK in the group treated with the candidate substance and the control. When the expression ratio of p-AMPK/AMPK in the group treated with the candidate substance is decreased compared to that of the control, the candidate substance may be determined as a drug for preventing muscular atrophy.

With respect to indicator (3) above, the degree of muscular atrophy may be evaluated by comparing expression ratios of p-Akt1/Akt1 in the group treated with the candidate substance and the control. When the expression ratio of p-Akt1/Akt1 in the group treated with the candidate substance is increased compared to that of the control, the candidate substance may be determined as a drug for preventing muscular atrophy.

With respect to indicator (4) above, the degree of muscular atrophy may be evaluated by comparing expression ratios of p-S6K/S6K in the group treated with the candidate substance and the control. When the expression ratio of p-S6K/S6K in the group treated with the candidate substance is increased compared to that of the control, the candidate substance may be determined as a drug for preventing muscular atrophy.

With respect to indicator (5) above, the degree of muscular atrophy may be evaluated by comparing expression ratios of p-FoxO1/FoxO1 in the group treated with the candidate substance and the control. When the expression ratio of p-FoxO1/FoxO1 in the group treated with the candidate substance is increased compared to that of the control, the candidate substance may be determined as a drug for preventing muscular atrophy.

With respect to indicator (6) above, the degree of muscular atrophy may be evaluated by comparing expression ratios of p-FoxO3/FoxO3 in the group treated with the candidate substance and the control. When the expression ratio of p-FoxO3/FoxO3 in the group treated with the candidate substance is increased compared to that of the control, the candidate substance may be determined as a drug for preventing muscular atrophy.

With respect to indicator (7) above, the degree of muscular atrophy may be evaluated by comparing expression levels of MuRF1 in the group treated with the candidate substance and the control. When the expression level of MuRF1 in the group treated with the candidate substance is decreased compared to that of the control, the candidate substance may be determined as a drug for preventing muscular atrophy.

With respect to indicator (8) above, the measurement of the activity of proteasome is the same as that of (h) described above, and the degree of muscular atrophy may be evaluated by comparing activities of proteasome in the group treated with the candidate substance and the control. When the activity of proteasome in the group treated with the candidate substance is decreased compared to that of the control, the candidate substance may be determined as a drug for preventing muscular atrophy.

With respect to indicator (9) above, the degree muscular atrophy may be evaluated by comparing expression levels of hot shock protein 72 (HSP72) in the group treated with the candidate substance and the control. When the expression level of hot shock protein 72 (HSP72) in the group treated with the candidate substance is increased compared to that of the control, the candidate substance may be determined as a drug for preventing muscular atrophy.

With respect to indicator (10) above, the degree of muscular atrophy may be evaluated by comparing expression levels of αB-crystallin in the group treated with the candidate substance and the control. When the expression level of αB-crystallin in the group treated with the candidate substance is increased compared to that of the control, the candidate substance may be determined as a drug for preventing muscular atrophy.

The expression levels of AMPK, phospho-AMPK (p-AMPK), FoxO1, p-FoxO1, FoxO3, p-FoxO3, Akt1, p-Akt1, S6K, p-S6K, MuRF1, HSP72, and αB-crystallin proteins The expression levels in (2) to (7), (9), and (10) may be measured using methods known as a protein analysis method. For example, the expression levels may be measured by immunoblotting.

Therefore, in the determining, when the group treated with the candidate substance is compared to the control, in the case of at least one result selected from the group consisting of an increase in size of myotubes or size of muscle; a decrease in expression ratio of p-AMPK/AMPK; an increase in expression ratio of p-Akt1/Akt1; an increase in expression ratio of p-S6K/S6K; an increase in expression ratio of p-FoxO1/FoxO1; an increase in expression ratio of p-FoxO3/FoxO3; a decrease in expression level of MuRF1; a decrease in activity of proteasome; an increase in expression level of heat shock protein 72 (HSP72); and an increase in expression level of αB-crystallin, the candidate substance may be determined as a drug for preventing muscular atrophy.

The control refers to a group treated with an excipient of the drug for preventing muscular atrophy instead of the candidate substance, and for example, the control may be a group consisting of dimethyl sulfoxide (DMSO), physiological saline, sterilized distilled water, carboxymethyl cellulose or phosphate buffered saline (PBS).

In the present specification, the normal cells or the normal animal refer to cells or animals without muscular atrophy.

For example, the animal may be an animal that is the same species as the muscular atrophy model and does not have muscular atrophy raised in the same or similar environment.

The present invention provides a pharmaceutical composition for preventing or treating muscular hypertrophy, containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

In one embodiment of the present invention, the hypometabolism-inducing substance may be more particularly 3-iodothyronamine (T1AM).

In one embodiment of the present invention, the muscular hypertrophy includes myotonia congenital, calf hypertrophy, myhre syndrome, and myostatin-related muscular hypertrophy.

In one embodiment of the present invention, since the hypometabolism-inducing substance of the present invention induces muscular atrophy by inhibiting activity of Akt1-S6K involved in muscle protein synthesis and activating FoxO-proteasome involved in muscle protein degradation, the hypometabolism-inducing substance can be used as a drug which may replace the role of myostatin and may be used for treatment of various muscle hypertrophies including myostatin-related muscular hypertrophy caused by binding of myostatin.

The present invention includes all of its pharmaceutically acceptable salt and solvates, hydrates, racemates, or stereoisomers capable of being prepared therefrom as well as the hypometabolism-inducing substance of the present invention.

The hypometabolism-inducing substance of the present invention may be used in a form of its pharmaceutically acceptable salt and as the salt, acid additional salts formed by free pharmaceutically acceptable acid are useful. The acid additional salts are obtained from inorganic acids such as hydrochloric acid, nitric acid, phosphoric acid, sulfuric acid, hydrobromic acid, hydriodic acid, nitrous acid or phosphorous acid and non-toxic organic acids such as aliphatic mono and dicarboxylate, phenyl-substituted alkanoate, hydroxy alkanoate and alkandioate, aromatic acids, aliphatic and aromatic sulfonic acids. The pharmaceutically non-toxic salt includes sulfate, fatigue sulfate, bisulfate, sulfite, bisulfite, nitrate, phosphate, mono-hydrogen phosphate, dihydrogen phosphate, meta-phosphate, pyrophosphate chloride, bromide, iodide, fluoride, acetate, propionate succinate, decanoate, caprylate, acrylate, formate, isobutyrate, caprate, heptanoate, propionic oleate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, hydroxybutyrate, glycollate, maleate, tartrate, methanesulfonate, propanesulfonate, naphthalene-1-sulfonate, naphthalene-2-sulfonate or mandelate.

The acid additional salt according to the present invention may be prepared by a general method, for example, dissolving the hypometabolism-inducing substance of the present invention in a large amount of acid aqueous solution and precipitating the salt by using a water-miscible organic solvent, for example, methanol, ethanol, acetone, or acetonitrile. Further, the salt which is dried or precipitated by evaporating the solvent or a large amount of acid from the mixture may also be prepared through suction-filtering.

Further, a pharmaceutically acceptable metal salt may be prepared by using base. An alkali metal or alkaline earth metal salt is obtained by, for example, dissolving the compound in a large amount of alkali metal hydroxide or alkaline earth metal hydroxide solution and filtering an insoluble compound salt and then evaporating and drying a filtrate. In this case, the metal salt is pharmaceutically suitable to prepare sodium, potassium or calcium salts. Further, the silver salt corresponding thereto is obtained by reacting alkali metal or alkaline earth metal salts with an appropriate silver salt (for example, silver nitrate).

When the composition is formulated, the formulation is prepared by using diluents or excipients, such as a filler, an extender, a binding agent, a wetting agent, a disintegrating agent, and a surfactant, which are generally used.

A solid formulation for oral administration includes a tablet, a pill, a powder, a granule, a capsule, a troche agent, or the like, and the solid formulation may be prepared by mixing at least one excipient, for example, starch, calcium carbonate, sucrose or lactose, gelatin, or the like with at least one hypometabolism-inducing substance of the present invention. Further, lubricants such as magnesium stearate talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin, as simple diluents which are commonly used.

A formulation for parenteral administration includes a sterile aqueous solution, a non-aqueous solution, a suspension, an emulsion, a lyophilizing agent, a suppository, and the like.

As the non-aqueous solution and the suspension, propylene glycol, polyethylene glycol, vegetable oils such as olive oil, injectable ester such as ethyl oleate, and the like may be used. As a matter of the suppository, witepsol, macrogol, tween 61, cacao butter, laurin, glycerol, gelatin, and the like may be used.

The composition according to the present invention is administered with a pharmaceutically effective dose. In the present invention, the "pharmaceutically effective dose" refers to a amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a route of administration, and an emission rate, duration of treatment, and simultaneously used drugs and other elements well-known in the medical field. The composition of the present invention may be administered as an individual therapeutic agent or administered in combination with other therapeutic agents, sequentially or simultaneously administered with existing therapeutic agents, and administered singly or multiply. It is important to administer an amount capable of obtaining a maximum effect with a minimal amount without side effects by considering the above elements and the amount may be easily determined by those skilled in the art.

Particularly, the effective dose of the composition according to the present invention may vary according to age, gender, and weight of the patient, and generally administered by 0.1 mg to 100 mg per weight 1 kg, preferably administered by 0.5 mg to 10 mg daily or every other day, or administered one to three times per day. However, since the effective dose may be decreased or increased depending on the route of administration, the severity of obesity, gender, weight, age, and the like, the dose is not limited to the scope of the present invention in any way.

The present invention provides a health food for preventing or treating muscular hypertrophy, containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

In one embodiment of the present invention, since the hypometabolism-inducing substance of the present invention induces muscular atrophy by inhibiting activity of Akt1-S6K involved in muscle protein synthesis and activating FoxO-proteasome involved in muscle protein degradation, the hypometabolism-inducing substance can be used as a drug which may replace the role of myostatin and may be used for health foods for preventing or improving various muscle hypertrophies including myostatin-related muscular hypertrophy caused by binding of myostatin.

Kinds of foods which are added with the hypometabolism-inducing substance of the present invention are not particularly limited. Examples of the foods which may be added with the materials include drinks, meat, sausages, bread, biscuits, rice cakes, chocolate, candies, snacks, cookies, pizza, ramen noodles, other noodles, gums, dairy products including ice cream, various soups, beverages, alcohol drinks, vitamin complex, milk products, milk dairy products, and the like, and include all health functional foods in the accepted meaning.

The hypometabolism-inducing substance of the present invention may be added to the food as it is or may be used together with other food or food ingredients, and may be appropriately used according to general methods. A mixing amount of active ingredients may be appropriately determined according to a purpose of use (for prevention or improvement) thereof. Generally, the amount of compound in the health functional food may be added with 0.1 to 90 parts by weight with respect to the entire food weight. However, in the case of long-term administration for health and hygiene or health control, the amount may be the range or less. Since there is no problem in terms of safety, the active ingredients may be used with the amount in the range or more.

In the health food composition according to the present invention, other ingredients are not particularly limited invention, other ingredients are not particularly limited except for containing the compound as the required ingredient at the indicated ratio, and like a general beverage, various flavoring agents, natural starches, or the like may be contained as an additional ingredient. Examples of the aforementioned natural carbohydrates include general sugars, such as monosaccharides, for example, glucose, fructose, and the like; disaccharides, for example, maltose, sucrose, and the like; and polysaccharides, for example, dextrin, cyclodextrin, and the like, and sugar alcohols, such as xylitol, sorbitol, and erythritol. As the flavoring agent other than the above examples, natural flavoring agents (thaumatin, stevia extract (e.g., rebaudioside A, glycyrrhizin, etc.) and synthetic flavoring agents (saccharin, aspartame, etc.) may be advantageously used. A ratio of the natural carbohydrate may be generally about 1 to 20 g and preferably about 5 to 10 g per 100 g of the composition of the present invention.

Further, the health food composition according to the present invention may contain various nutrients, vitamins, minerals (electrolytes), flavoring agents such as synthetic flavoring agents and natural flavoring agents, coloring agents and thickening agents (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like. Besides, the health food composition of the present invention may include pulps for preparing natural fruit juice and fruit juice drinks, and vegetable drinks.

These ingredients may be used independently or in combination. The ratio of such additives is not limited, but is generally selected in the range of 0.1 to about 20 parts by weight per 100 parts by weight of the hypometabolism-inducing substance of the present invention.

Further, the present invention provides a pharmaceutical composition for facial muscle shrinkage containing a hypometabolism-inducing substance of the present invention as an active ingredient.

In one embodiment of the present invention, since the hypometabolism-inducing substance of the present invention induces muscular atrophy by inhibiting activity of Akt1-S6K involved in muscle protein synthesis and activating FoxO-proteasome involved in muscle protein degradation, the hypometabolism-inducing substance may be usefully used as the composition for facial muscle shrinkage which may be used for Botox.

Hereinafter, the present invention will be described in more detail through Experimental Examples according to the present invention, but the scope of the present invention is not limited to Experimental Examples to be described below and the like.

EXPERIMENTAL EXAMPLES

1. Experimental Substances and Method

1) Chemicals and Storage Solutions

T1AM was chemically synthesized (Korean Patent Registration No. 1,112,731) and dissolved in dimethyl sulfoxide (DMSO; SIGMA, Missouri, US) at a storage concentration of 0.75 and 1 M. A DMEM (Welgene, Dalseogu, Daegu, Korea) medium was used, and nonidet P-40, a complete mini protease inhibitor, and a phosphatase inhibitor cocktail were purchased from Roche. A RIPA buffer solution (1% Nonidet P-40, 1% sodium deoxycholate, 150 mM NaCl, 10 mM sodium phosphate [pH 7.4], 2 mM EDTA, 50 mM NaF, 0.2 mM $Na_3VO_4$, 40 mM HEPES [pH 7.4], 0.7% CHAPS, 1% SDS, and protease inhibitor cocktail) was used for protein extraction. An ECL system purchased from GE Healthcare (Fairfield, Conn., USA) and stored at 4 and a restore western blot stripping buffer purchased from Thermo Scientific (Rockford, Ill., USA) were used for immunoblot analysis. Rabbit anti-phospho-AMPK (at Thr172)), AMPK, phospho-FoxO1 (Ser256), FoxO1, phospho-FoxO3 (Ser253), FoxO3, HSP27, αB-crystallin, phosphor-S6K (Thr389), S6K, phospho-Akt1 (Ser473), and Akt1 polyclonal antibodies were purchased from Cell Signaling Technology (Beverly, Calif., USA) and used. Rabbit anti-muscle RING-finger protein-1 (MuRF1) and F-Box Only Protein 32 (MAFbx/atrogen) polyclonal antibody were purchased from Santa Cruz Biotechnology (Santa Cruz, Calif., USA) and used, and mouse anti-heat shock proteins (HSP) 90, 72, and 60 were purchased from Stressgen (Victoria, BC, Canada) and used. Mouse anti-glyceraldehydes-3-phosphate dehydrogenase (GAPDH) antibodies were purchased from Abcam (Cambridge, UK) and HRP-conjugated anti-mouse IgG and anti-rabbit IgG were purchased from Cell Signaling Technology and used.

2) Cell Culture

C2C12 myoblasts were purchased from American Type Culture Collection (Rockville, Md., USA) and cultured in a DMEM medium containing 4,500 mg/L glucose supplemented with 10% fetal bovine serum (Hyclone, Logan, Utah, USA) and 1% antibiotics/antimycotics Gibco, Burlington, Ontario, Canada). The myoblasts were stored under conditions of 37° C. and 5% $CO_2$. The myoblasts were grown on a 6-well culture plate for immunoblot analysis and measurement of diameters of myotubes. The myoblasts were maintained in each well for 5 days by replacing the medium with a differentiation medium (DMEM containing 2% horse serum and 1% antibiotics/antimycotics) at about 80% confluent state and induced to be differentiated into myotubes. The medium was replaced with a new medium every two days.

3) Measurement of Cell Size

To verify the effect of T1AM on the size of C2C12 myotubes, the cells were fixed with 4% paraformaldehyde and photographed at 200× magnification on an Axiovert 200 optical microscope. For analysis, the cells were divided into 9 fractions in order to randomly select the cells. The diameter of each myotube was measured using Image J software (NIH, Frederick, Md., USA).

4) Immunoblot Analysis

The cells were obtained with a RIPA buffer, degraded by repeated suction through a 21 gauge needle, and the transferred to a 1.5 mL microtube. A sample was cultured on ice for 5 minutes and centrifuged at 13,000 rpm at 4° C. for 10 minutes. A supernatant was obtained with whole-cell soluble lysates and the protein concentration was determined through Bradford assay. To detect AMPK, phospho-AMPK (p-AMPK), FoxO1, p-FoxO1, FoxO3, p-FoxO3, Akt1, p-Akt1, S6K, p-S6K, MuRF1, MAFbx, HSP90, HSP72, HSP60, HSP27, αB-crystallin, and GAPDH, a total of 30 μg of proteins was electrophoresed on 8 to 10% SDS-PAGE. The proteins were electrophoretically transferred from the gel to a nitrocellulose membrane. The membrane reacted with a blocking buffer (1×TBS, 0.5% Tween-20 with 5% w/v nonfat dry milk) for 1 hour at room temperature and then washed with 10 mL TBST three times every 10 minutes. Thereafter, the membranes reacted with a primary antibody diluted appropriately with 10 mL TBST (1:500 to 1:10,000) overnight at 4° C. The membrane reacted with a HRP-conjugated secondary antibody for detection of bound proteins in 10 mL TBST at room temperature for 1 hour by stirring and then washed with 10 mL TBST three times every 10 minutes. An immunocomplex was detected by the ECL system (GE Healthcare, Fairfield, Conn., USA) and the obtained bands were quantified by ImageJ 1.47t software (NIH, MD, USA). The protein density was normalized by the density of GAPDH. To detect the GAPDH, the membrane was washed with TBST three times for every 10 minutes and then cultured in a restore buffer for 30 minutes at room temperature to be stripped.

5) Immunofluorescence and Confocal Microscope

The cells on each 6-well plate were washed three times with 1× PBS and fixed with 4% paraformaldehyde for 30 minutes at room temperature. Thereafter, the cells were then treated with 0.2% Tritin X-100 for 10 minutes on ice to ensure permeability and blocked from the 1× PBS with 3% BSA. The cells were stained with primary antibodies against FoxO1 and FoxO3 diluted at 1:100 in 1× PBS, respectively, and reacted with Alexa 488-conjugated secondary antibody diluted at 1:1,000. Finally, the cells were washed three times with 1× PBS and then a mounting medium containing DAPI (Vector Laboratories, Burlingame, Calif., USA) was dropped on the cells. Fluorescent-labeled cells were detected with a Carl Zeiss LSM750 confocal microscope (Jena, Germany).

6) Analysis of Activity of 26S Proteasome

Two groups of myotubes were trypsinized and then washed with a fresh differentiation medium. Among three determinants of proteasome activities (trypsin-, chemotrypsin- and caspase-like activities), the chemotrypsin-like activity is regarded as representative of the protease capacity of the proteasome. The chemotrypsin-like activity was determined according to the manufacturer's protocol using a Promega Proteasome-Glo cell-based luminescence assay kit (Promega, Madison, Wis., USA) by approximately 7,500 cells measured by a cell counter (Bio-rad, Hercules, Calif., USA) in 50 μl of the differentiation medium. To confirm the specificity of the analysis, a partial sample containing the same number of cells was pretreated with a proteasome inhibitor, epoxomicin, at a concentration of 10 μM for 30 minutes. The chemotrypsin-like activity was measured by the same process and the result was used as a background signal for analysis. The luminescence was measured with a GloMax 20/20 Luminometer (Promega).

7) Statistical Analysis

All values corresponding to the measurement result were represented by mean±SEM. A difference between the groups in means for biochemical measurement (e.g., AMPK, Akt1, etc.) was verified by an independent sample t-test. Statistical analysis was performed using SPSS/PC+, and significance was determined at P=0.05.

2. Experimental Result

1) Muscular Atrophy Effect of T1AM in Muscle Cells

Figure 1:
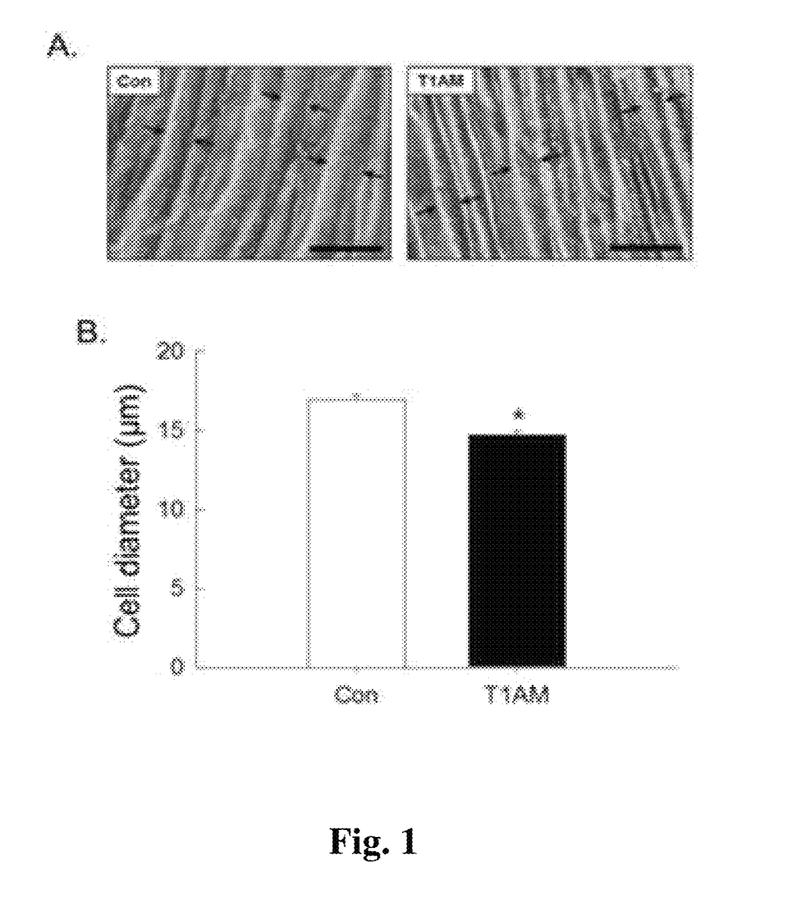
FIG. 1 illustrates comparison of diameters of C2C12 myotubes between a T1AM treated group and a control: A illustrates a representative photograph of myotubes taken with an Axiovert 200 optical microscope (magnification: 200×0, in which a pair of arrows indicates locations where diameters of the myotubes are measured (black bar=25 μm). B is a graph illustrated by measuring the diameters of myotubes between two groups. Data: Mean±SEM (n=3; 96 cells/group), *: It means that there is a significant difference between the two groups [independent samples t-test, $P<0.05$)].

To determine whether T1AM induced muscular atrophy in C2C12 myotubes, cells were photographed under a phase contrast microscope (FIG. 1A) and the diameter was measured at 200× magnification (FIG. 1B).

As a result, as shown in FIG. 1, it was shown that when 75 μM of T1AM was treated for 6 hours, the size of myotube was decreased by 0.13 times as compared to a vehicle control (16.97±0.32 m).

2) Increase in AMPK Phosphorylation in T1AM-Treated Cells

Figure 2:
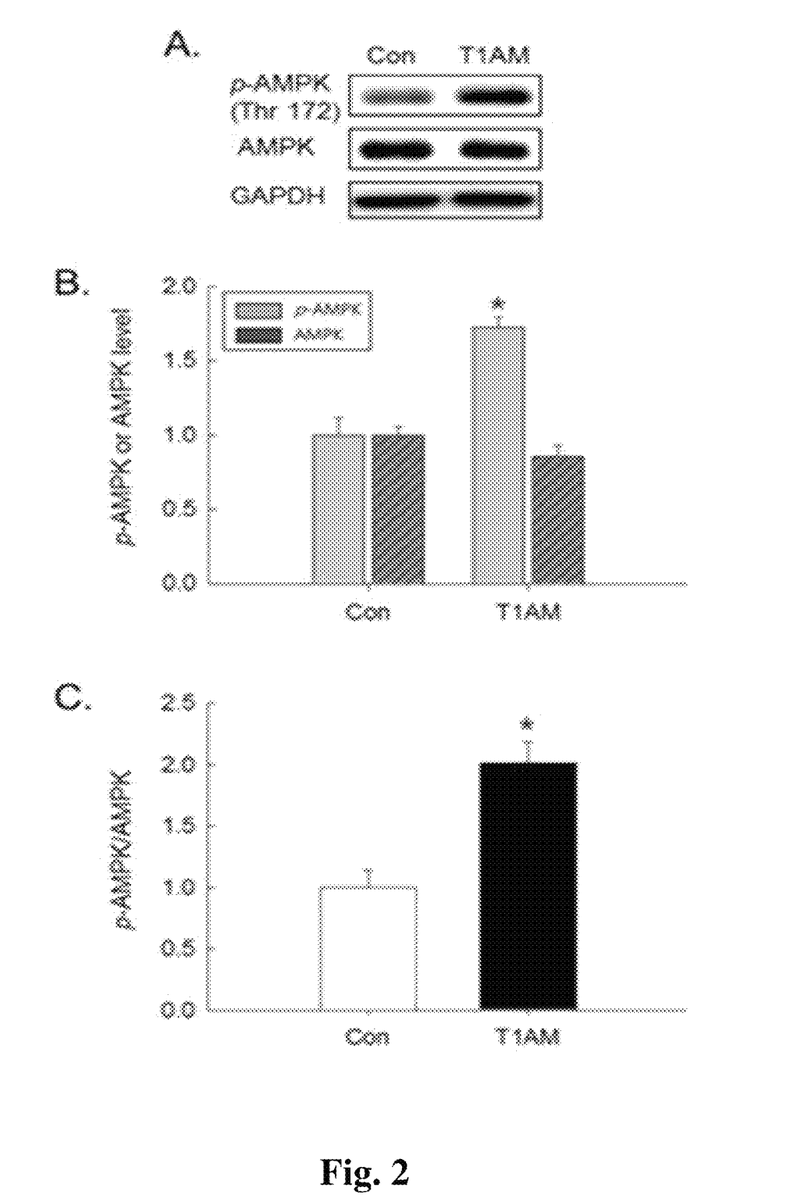
FIG. 2 illustrates comparison of AMPK activities of C2C12 myotubes between a T1AM treated group and a control: A illustrates a result of Immunoblotting analysis for expression of p-AMPK and AMPK. B is a graph illustrating expression levels of p-AMPK and AMPK as densitometric quantitation, and C is a graph illustrating an expression ratio of p-AMPK/AMPK as densitometric quantitation [mean±SEM (n=6), *, $P<0.05$].

As shown in FIG. 2, it was shown that the AMPK phosphorylation was remarkably increased (2.7 times) in the T1AM-treated group compared to the control in the immunoblotting analysis, whereas the total expression levels of AMPK were similar between the two groups. As a result, the expression ratio of p-AMPK/AMPK in the T1AM-treated group was 2.0 times higher than that of the control (FIG. 2C).

3) Down-Regulation of Anabolic Signaling Activity in T1AM-Treated Cells

Figure 3:
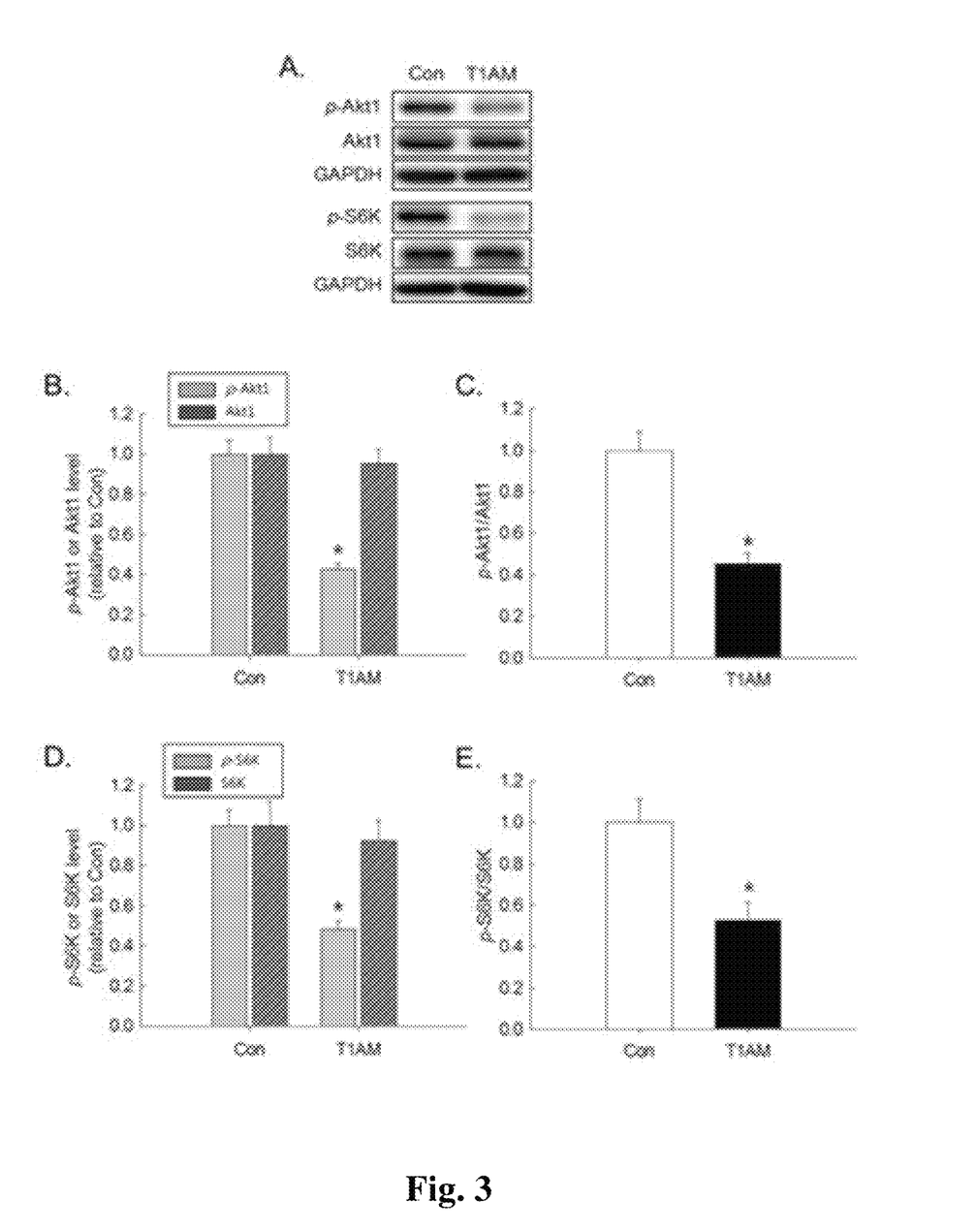
FIG. 3 illustrates comparison of expression of Akt1 and S6K of C2C12 myotubes between a T1AM treated group and a control: A illustrates a result of Immunoblotting analysis for expression of Akt1 and S6K. B and C are graphs illustrating expression levels of p-Akt1 and Akt1 and an expression ratio of p-Akt1/Akt1, respectively. D and E are graphs illustrating expression levels of p-S6K and S6K and an expression ratio of p-S6K/S6K, respectively [mean±SEM (n=6), *, $P<0.05$].

As shown in FIG. 3, it was shown that a phosphorylation level of Akt1 was significantly down-regulated in the T1AM-treated group compared to the control, but the non-phosphorylation level between the two groups was similar to each other. Accordingly, the expression ratio of p-Akt1/Akt1 in the T1AM-treated group was 0.45 times lower than that of the control (FIG. 3C). Further, the p-S6K level was lowered by T1AM treatment and as a result, the expression ratio of p-S6K/S6K in the T1AM-treated group was 0.53 times lower than that of the control (FIG. 3E).

4) Down-Regulation of p-FoxO1 and p-FoxO3 in T1AM Treated Cells

Figure 4:
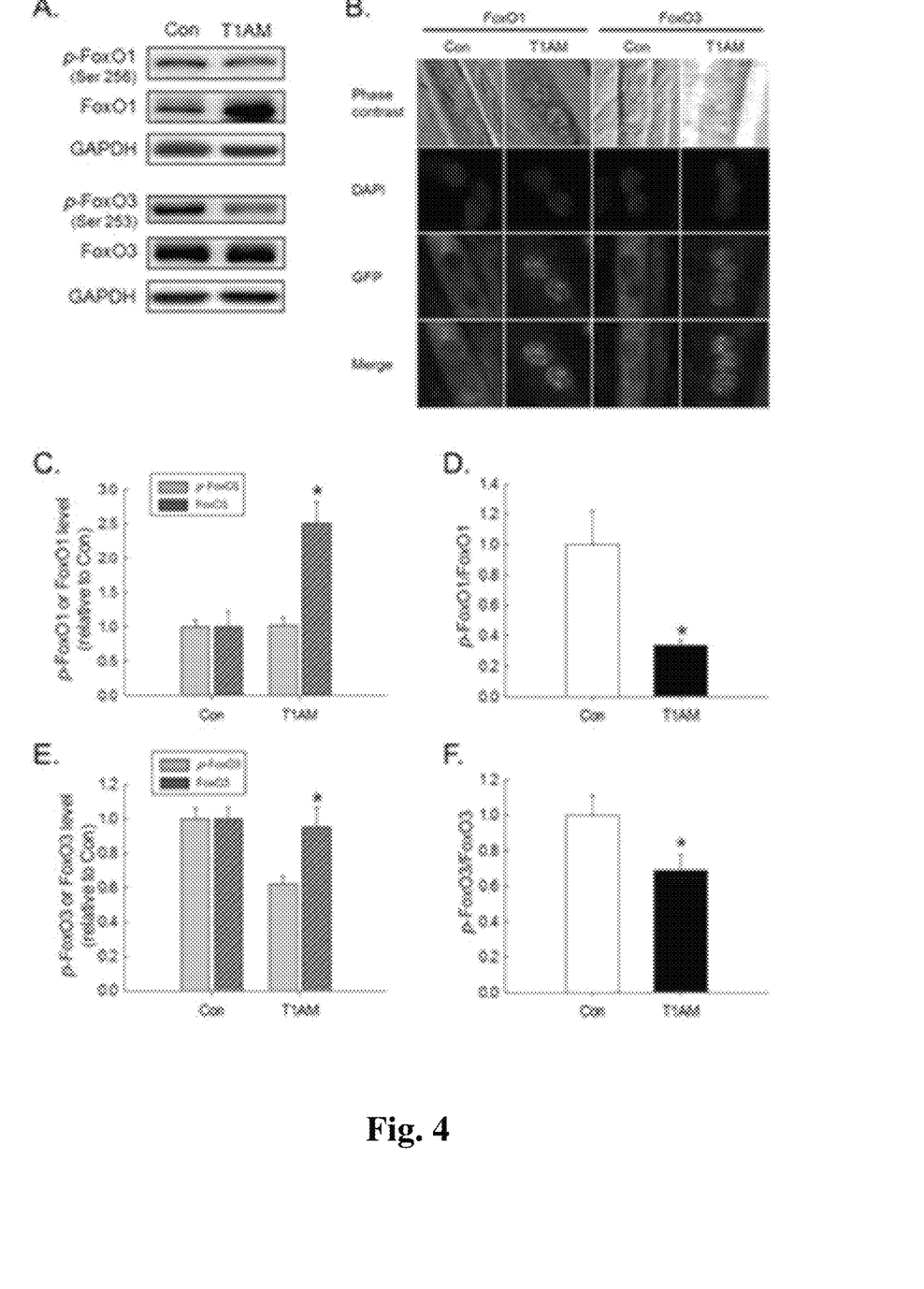
FIG. 4 illustrates comparison of expression of FoxO1 and FoxO3 of C2C12 myotubes between a T1AM treated group and a control: A illustrates a result of immunoblotting analysis for expression of FoxO1 and FoxO3. B is a photograph taken as an analysis result of immunofluorescence staining for FoxO1 and FoxO3 with a confocal microscope. C and D are graphs illustrating expression levels of p-FoxO1 and FoxO1 and an expression ratio of p-FoxO1/FoxO1, respectively. E and F are graphs illustrating expression levels of p-FoxO1 and FoxO1 and an expression ratio of p-FoxO3/FoxO3, respectively [mean±SEM (n=6), *, $P<0.05$].

As shown in FIG. 4, it was shown that the total expression of FoxO1 in the T1AM-treated group was 2.5 times higher than that of the control (in Ser256), whereas the phosphorylation level between the two groups was similar. It was shown that the expression ratio of p-FoxO1/FoxO1 was 0.66 times lowered in the T1AM-treated group (FIG. 4D). On the other hand, it was shown that the total expression of FoxO3 was not different between the T1AM-treated group and the control, but the p-FoxO3 level was 0.58 times lowered in the T1AM-treated group. Thus, the expression ratio of p-FoxO3/FoxO3 in the T1AM-treated group was 0.39 times lower than of the control (FIG. 4F).

5) Up-Regulation of MuRF1 Expression and Proteasome Activity

Figure 5:
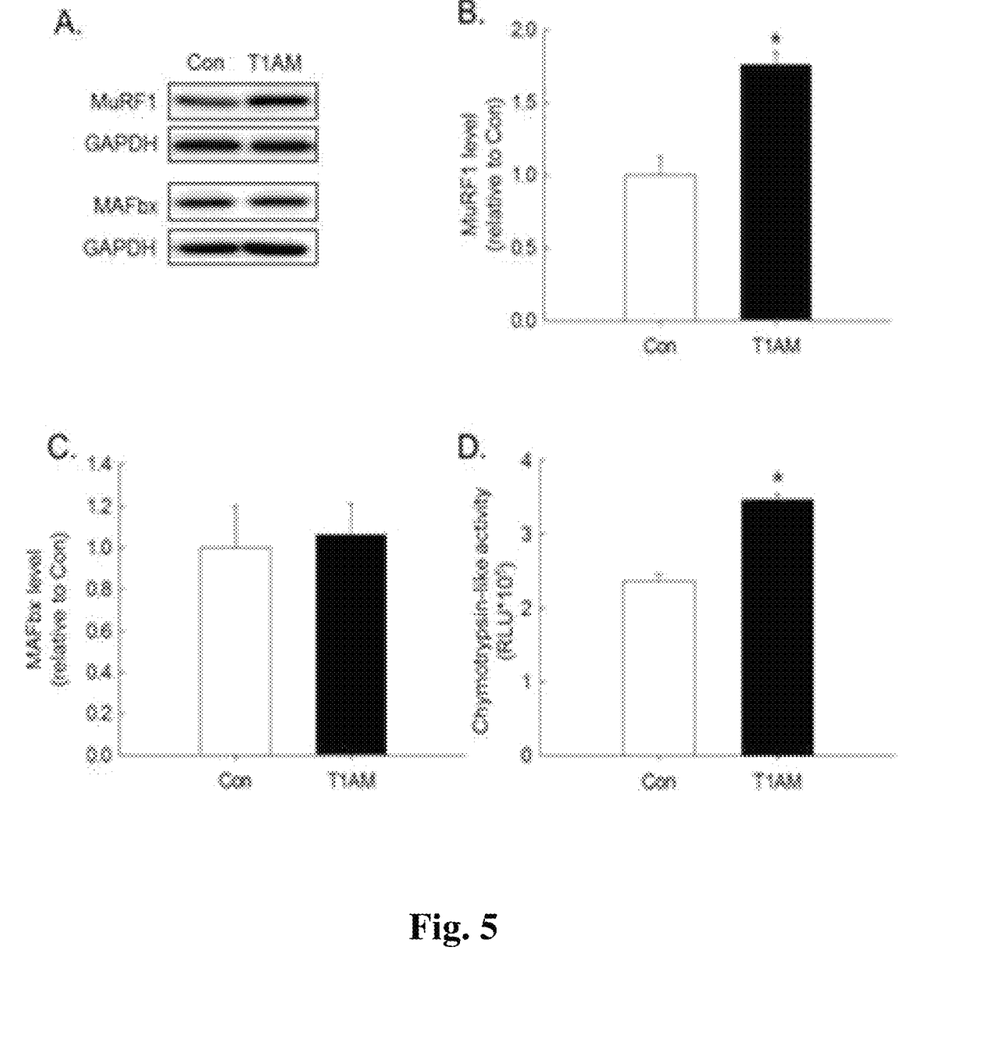
FIG. 5 illustrates comparison of expression of MuRF1 and MAFbx of C2C12 myotubes between a T1AM treated group and a control: A illustrates a result of immunoblotting analysis for expression of FoxO1 and FoxO3. B and C are graphs illustrating densitometric quantitation for expression levels of MuRF1 and MAFbx. D illustrates chymotrypsin-like activity of 26S, which is determined through cell-based luminescence analysis and expressed as a relative light unit (RLU). Actual chymotrypsin-like activity was determined from <total RLUs-background RLUs> in each analysis [mean±SEM (n=6), *, $P<0.05$].

As shown in FIG. 5, among experimented catabolic signaling markers, the expression of MuRF1 in the T1AM-treated group was 1.8 times higher than that in the control (FIGS. 5A and 5B), whereas the expression of MAFbx was not affected by the T1AM treatment (FIGS. 5A and 5C). The chymotrypsin-like activity, one of the major catabolic properties of proteasome, in the T1AM-treated group was 1.5 times higher than that of the control (FIG. 5D).

6) Decrease in Expression of HSP72 and αB-Crystallin in T1AM Treated Cells

Figure 6:
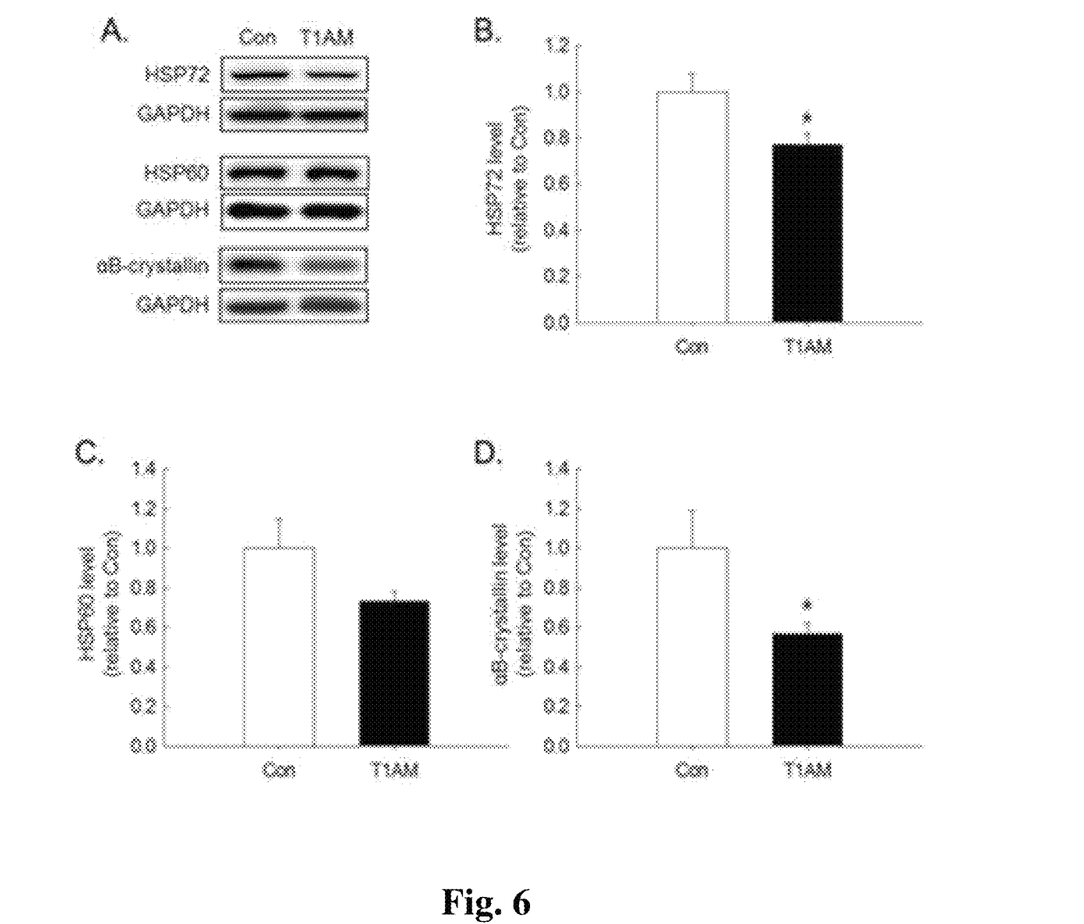
FIG. 6 illustrates comparison of expression of chaperone of C2C12 myotubes between a T1AM treated group and a control: A illustrates a result of immunoblotting analysis of expression of heat shock protein 72 (HSP72), HSP60 and αB-crystallin. B and D are graphs illustrating densitometric quantitation for an expression level of each chaperone protein [mean±SEM (n=6), *, $P<0.05$].
Figure 7:
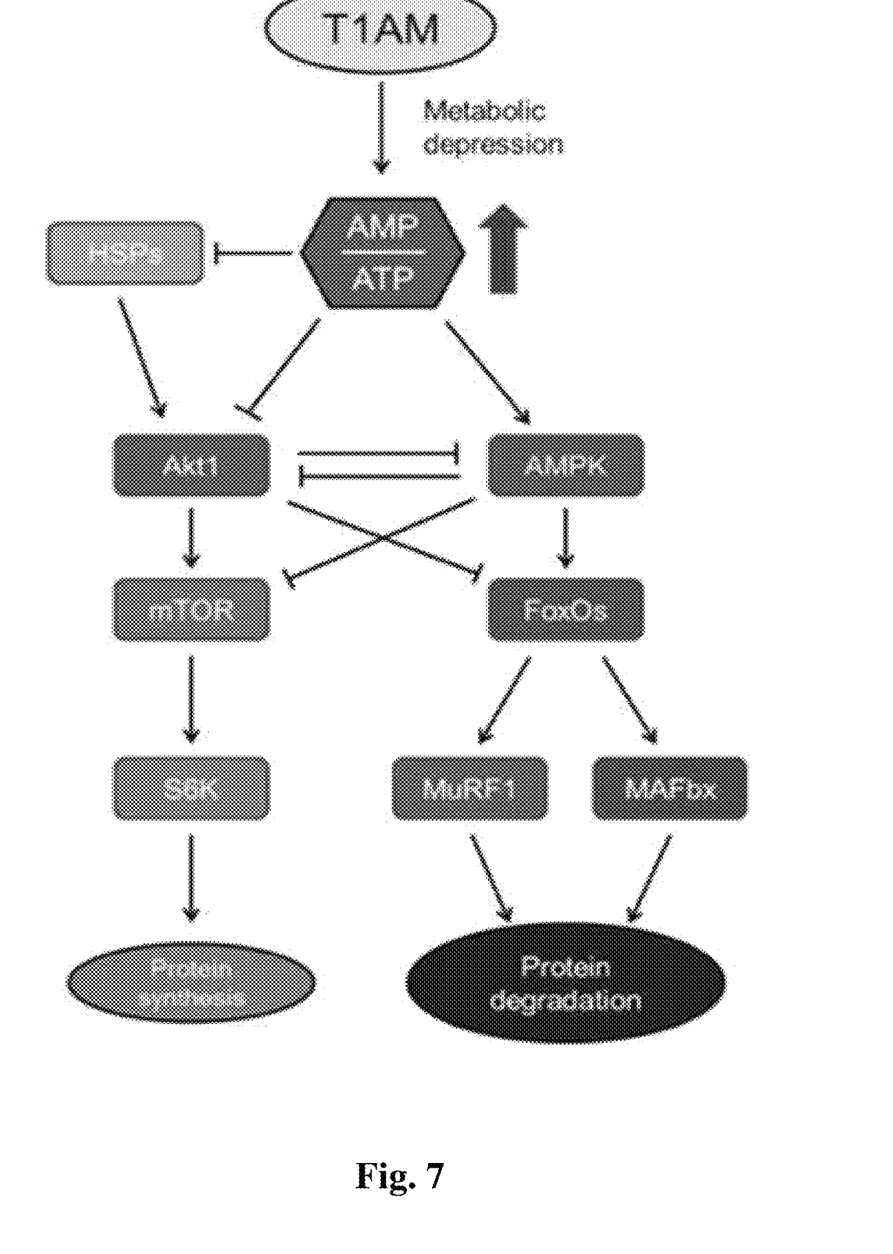
FIG. 7 is a schematic diagram of signaling pathways associated with synthesis and degradation of muscle proteins according to T1AM treatment.

As shown in FIG. 6, it was shown that the expression levels of HSP72 and αB-crystallin in the T1AM-treated group were 0.89 times and 0.63 times down-regulated compared to the control, whereas a difference in HSP60 expression between the two groups was not statistically significant.

3. Conclusion

The activity of FoxOs is known to be regulated by an antagonistic effect of AMPK and Akt1. That is, a decrease in expression ratio of p-FoxO/FoxO corresponds to up-regulated p-AMPK and corresponds to down-regulated p-Akt1. This induces protein degradation as one of the catabolism. As seen from the above experimental results, AMPK, FoxO1, FoxO3, MuRF1 and proteasome involved in the muscle protein degradation mechanism are activated by T1AM mediated hypometabolism, whereas AKT1, S6K, heat shock protein 72 (HSP72), and αB-crystallin involved in the muscle protein synthesis mechanism are inactivated. Therefore, the hypometabolism-inducing substance according to the present invention, particularly T1AM, induces hypometabolism to inhibit energy metabolism and activating the catabolism, thereby activating the protein associated with the muscle protein degradation mechanism and inhibiting the proteins associated with the muscle protein synthesis mechanism, and as a result, the sizes of the myoblasts are decreased.

The invention claimed is:

1. A method for preparing a muscular atrophy study model, the method comprising:
   1) administering a hypometabolism-inducing substance 3-iodothyronamine (T1AM) to normal myotubes or to a normal animal intraperitoneally,
   2) determining the following characteristic of the normal myotubes of the step 1) or myotubes isolated from the animal of the step 1)], compared to normal myotubes:
   a decrease in size of the myotubes;
   an increase in an expression ratio of p-AMPK/AMPK;
   a decrease in an expression ratio of p-Akt1/Akt1;
   a decrease in an expression ratio of p-S6K/S6K;
   a decrease in an expression ratio of p-FoxO1/FoxO1;
   a decrease in an expression ratio of p-FoxO3/FoxO3;
   an increase in an expression level of MuRF1;
   an increase in an activity of proteasome;
   a decrease in an expression level of heat shock protein 72 (HSP72); and
   a decrease in an expression level of αB-crystallin.

2. The method of claim 1, wherein a dose of the 3-iodothyronamine (T1AM) is 0.1 μM to 1000 μM in the case of the myotubes, and 10 to 500 mg/kg per unit weigh (kg) of the animal in the case of the animal.

3. The method of claim 1, wherein in the study model, the animal is a vertebrate.

4. The method of claim 1, wherein a degree of muscular atrophy is adjusted in proportion to a dose of the T1AM; or an exposure time in vivo of the T1AM.

5. The method of claim 1, wherein when 0.1 μM to 1000 μM of the T1MA is administered in step 1), in step 2) the following characteristic of the myotubes of the step 1) or the myotubes isolated from the animal of the step 1) is determined in comparison to the normal myotubes:
   0.01 to 0.20 times decrease in size of the myotubes;
   0.5 to 2.5 times increase in the expression ratio of p-AMPK/AMPK;
   0.1 to 1.0 times decrease in the expression ratio of p-Akt1/Akt1;
   0.1 to 1.0 times decrease in the expression ratio of p-S6K/S6K;
   0.1 to 1.5 times decrease in the expression ratio of p-FoxO1/FoxO1;
   0.1 to 0.8 times decrease in the expression ratio of p-FoxO3/FoxO3;
   0.1 to 2.5 times increase in the expression level of MuRF1;
   0.01 to 2.0 times increase in the activity of proteasome;
   0.01 to 0.15 times decrease in the expression level of heat shock protein 72 (HSP72); and
   0.01 to 1.0 times decrease in the expression level of αB-crystallin.

* * * * *